(12) United States Patent
Lee et al.

(10) Patent No.: US 8,869,266 B2
(45) Date of Patent: Oct. 21, 2014

(54) MANAGEMENT SYSTEM OF TEST DEVICE AND MANAGEMENT METHOD THEREOF

(75) Inventors: Jong Rip Lee, Bucheon-si (KR); Seock Woo Jang, Suwon-si (KR); Seok Ho Kim, Bucheon-si (KR); Sung Hwa Lee, Anyang-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 114 days.

(21) Appl. No.: 13/335,060

(22) Filed: Dec. 22, 2011

(65) Prior Publication Data

US 2012/0167203 A1 Jun. 28, 2012

(30) Foreign Application Priority Data

Dec. 22, 2010 (KR) .................. 10-2010-0132598

(51) Int. Cl.
*G06F 15/00* (2006.01)
*G06F 19/00* (2011.01)

(52) U.S. Cl.
CPC .................. *G06F 19/366* (2013.01)
USPC ............. 726/19; 726/6; 702/182; 702/183; 702/188

(58) Field of Classification Search
CPC ................................ G06F 19/366
USPC ................ 726/6, 19; 702/182, 183, 188
See application file for complete search history.

(56) References Cited

U.S. PATENT DOCUMENTS

| | | | |
|---|---|---|---|
| 6,480,762 B1* | 11/2002 | Uchikubo et al. | 700/253 |
| 6,792,396 B2* | 9/2004 | Inda et al. | 702/188 |
| 7,085,669 B2* | 8/2006 | Isami | 702/127 |
| 7,451,064 B2* | 11/2008 | Hodge et al. | 702/187 |
| 7,757,117 B2* | 7/2010 | Mittal et al. | 714/15 |
| 7,979,238 B2* | 7/2011 | Fienblit et al. | 702/182 |
| 8,301,412 B2* | 10/2012 | Green et al. | 702/182 |
| 8,346,574 B2* | 1/2013 | Chirica et al. | 705/3 |
| 8,447,568 B2* | 5/2013 | Doddek et al. | 702/183 |
| 8,595,041 B2* | 11/2013 | Schmidt | 705/7.11 |
| 2003/0023709 A1* | 1/2003 | Alvarez et al. | 709/223 |
| 2006/0059018 A1* | 3/2006 | Shiobara et al. | 705/2 |
| 2008/0215366 A1* | 9/2008 | Robson et al. | 705/2 |

FOREIGN PATENT DOCUMENTS

| | | |
|---|---|---|
| JP | 11-154195 A | 6/1999 |
| JP | 2002-132925 A | 5/2002 |

* cited by examiner

*Primary Examiner* — Kambiz Zand
*Assistant Examiner* — Tongoc Tran
(74) *Attorney, Agent, or Firm* — Sughrue Mion, PLLC

(57) ABSTRACT

Assigning identifiers to a plurality of test devices to manage the test devices, and displaying the assigned identifiers on the test devices to distinguish the test devices.

13 Claims, 5 Drawing Sheets

FIG. 4

| Type | Address | Device | Serial No. | Status |
|------|---------|--------|------------|--------|
| LAN | 10.240.87.158 | A | C001M1ASA00... | OnLine |
| | | | | |
| | | | | |
| | | | | |
| | | | | |
| | | | | |
| | | | | |

Device List

MANAGEMENT SYSTEM OF TEST DEVICE AND MANAGEMENT METHOD THEREOF

CROSS-REFERENCE TO RELATED APPLICATION

This application claims priority from Korean Patent Application No. 10-2010-0132598, filed on Dec. 22, 2010, in the Korean Intellectual Property Office, the disclosure of which is incorporated herein by reference in its entirety.

BACKGROUND

1. Field

Methods and apparatuses consistent with the exemplary embodiments relate to a management system for a plurality of test devices required for examination of biomaterials and a management method thereof.

2. Description of the Related Art

A number of medical instruments used for clinical diagnosis including, for example, devices for testing and analyzing various biomaterials, have recently been decreased in size and weight. With a tendency of decreasing a size and/or weight of the medical instruments, a greater number and various kinds of medical instruments can now be used in the same space, compared to the prior art. Information measured by numerous medical instruments is transported and managed by a management system for such medical instruments.

As the number and type of medical instruments increase, understanding the correct one among the medical instruments, from which the results collected by the management system have been transmitted, becomes increasingly difficult. In order to distinguish the medical instruments, serial numbers for individuals or specified marks for users thereof alone must be remembered to identify the medical instruments. However, such methods depend upon the memory of the user, in turn being unreliable and causing a problem of inconvenience. Further, if individual users have different styles to distinguish specific medical instruments, a problem in communication between users may also be encountered. Accordingly, more convenient methods for easily distinguishing a plurality of medical instruments are still required.

SUMMARY

According to aspects of the exemplary embodiments, there are provided a management system that manages a plurality of test devices by providing an identifier to each of the devices, and a management method for the same.

A management system according to an aspect of an exemplary embodiment, a system for managing a plurality of test devices may include: a management device that assigns a first identifier to a first test device among the plurality of test devices and a second identifier to a second test device among the plurality of test devices, wherein the first test device displays the first identifier and the second test device displays the second identifier.

The management device may store a management program that manages the plurality of test devices.

The identifier is different from the second identifier and the first identifier and the second identifier are registered in the management device by the management program.

The identifier may be a mark for distinguishing the plural test devices from one another.

The test device may be a test device that analyzes biomaterials.

The test device may have the identifier assigned by the management device, and the assigned identifier may be displayed on a display part of the test device.

Communication between the management device and the test device may be performed any one of Bluetooth, infrared ray communication, Wi-Fi, wired or wireless communication over a network, Serial, ZigBee, RF and USB.

According to an aspect of an exemplary embodiment, there may be provided an method of managing a plurality of test devices, including: selecting, by a management system, a test device present on a network of the management system; providing an identifier to the selected test device; associating the provided identifier with identification information of the test device; and storing the associated information in the management system.

The selecting may include: locating the test device on the network; and selecting the identifier, wherein the identifier is a unique identifier.

The selecting may include: selecting the identifier; and connecting the test device, and wherein the providing comprises providing the selected identifier to the connected test device.

The connecting may include: attempting a connection to the test device; requesting input of a password; and, in response to receiving the requested password, permitting the connection to the test device.

The password may be a secret code that is requested to be input when settings of the test device are changed.

The test device may display the identifier assigned to the test device on an indication part of the test device.

According to one or more aspects of the exemplary embodiments, providing identifiers on respective test devices and indicating the same on the test devices, respectively, may enable more convenient and effective management of the test devices.

BRIEF DESCRIPTION OF THE DRAWINGS

These and/or other aspects of the exemplary embodiments will become apparent and more readily appreciated from the following description of the exemplary embodiments, taken in conjunction with the accompanying drawings of which:

FIG. 4 illustrates provision of an identifier to a test device according to an exemplary embodiment.

DETAILED DESCRIPTION OF EXEMPLARY EMBODIMENTS

Figure 1:
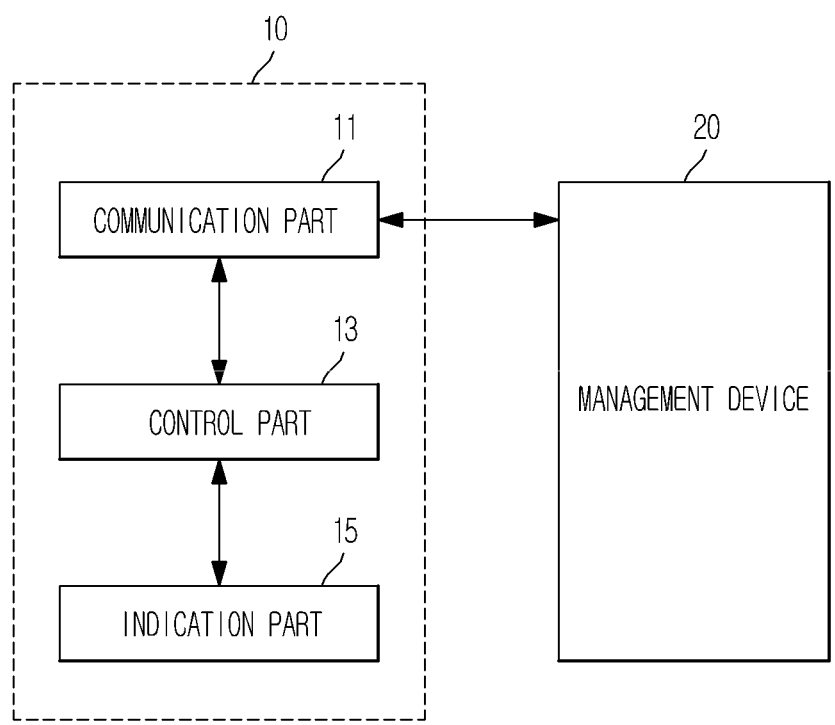
FIGS. 1 and 2 are block diagrams illustrating the configuration of a management system for a test device according to an exemplary embodiment.

Hereinafter, features and characteristics of the present disclosure and practical methods thereof will be clearly understood through the following detailed description of exemplary embodiments with reference to the accompanying drawings. However, at least one exemplary embodiment of the present disclosure may be embodied in various other forms, which are not particularly restricted to those described herein.

In the accompanying drawings, like reference numerals denote elements substantially having the same configurations or performing similar functions and actions throughout the drawings.

Figure 2:
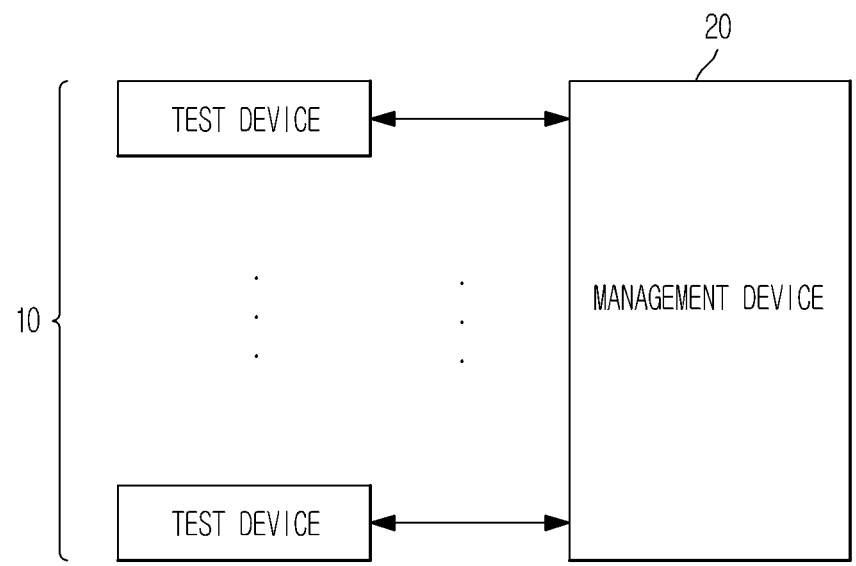

FIGS. 1 and 2 are block diagrams illustrating the configuration of a management system for a test device according to an exemplary embodiment.

The management system may include a test device 10, which performs analysis or testing of a biomaterial, and a management device 20 that manages the test device 10.

The test device 10 is a device that analyzes and/or tests various samples and, according to a kind of the sample, the test device 10 may be provided in a plurality of types.

Here, the sample may be any one selected from among a group consisting of DNA, oligonucleotides, RNA, PNA, ligand, receptor, antigen, antibody, milk, urine, saliva, hair, a crop sample, a meat sample, a bird sample, a livestock sample, a processed food sample, buccal cells, a tissue sample, sperm, protein or other biomaterials, without being particularly limited thereto. On the other hand, examples of analyte may include protein, antigen, antibody, DNA, RNA, oligonucleotides, receptors, or the like, without being particularly limited thereto. For instance, in the case where urine is used as a test sample, the analyte may be blood, glucose, ascorbic acid, ketone, protein, sugar, urobilinogen, bilirubin, and so forth. The above-described samples are merely exemplary, and the skilled artisan will understand that other samples may be provided.

Hereinafter, the following description will be given of illustrating a blood testing apparatus as an example of a test device for analyzing blood. However, the present disclosure is not particularly limited thereto, and the skilled artisan will understand that various sample testing devices could be provided.

As shown in FIG. 1, a test device 10 has an indication part 15 that displays a condition of the device and enables a user to know the same, a communication part 11 that communicates with the management device 20, and a control part 13 that controls overall functions of the test device 10.

The indication part 15 may indicate different states of an apparatus using characters, text or images to allow the user to recognize the states. Alternatively, the indication part 15 may output an audio indication.

The indication part 15 may be, for example, a touch-screen. When the user directly touches input buttons indicated on the indication part 15 with a hand (or finger), a variety of information for operation of the device may be input, in turn operating the device according to the information. That is, the indication part 15 may not only display the status of the device to the outside, but also serve as an input part, to which instructions are input to execute functions of the device. Of course, an input part having several input buttons formed thereon may be additionally provided. As one illustrative example of operating the indication part 15, the touch-screen was described. However, the indication part 15 is not particularly limited thereto.

The communication part 11 communicates with the management device 20. The communication part 11 transmits information, such as analysis and/or test results of various biomaterials, to the management device 20, which in turn are managed in the management device 20. In addition, the communication part may receive information, such as management information including software updates for the test device 10, from the management device 20, enabling management of the test device 10.

Communication between the communication part 11 and the management device 20 may be performed by Bluetooth, infrared communication, Wi-Fi, wired (Ethernet)/wireless (IEEE 802.11.x) communication in a network, Serial, Zig-Bee, RF and/or Universal Serial Bus (USB) communication, without being particularly limited thereto.

The control part 13 may be a microcomputer (e.g., central processing unit, microprocessor, etc.) controlling overall functions of the test device 10 according to an input signal transmitted from the indication part 15 or an alternative input part (not shown).

The control part 13 may store a password of the test device 10 in a memory (e.g., RAM, ROM, etc.) (not shown) of the test device 10 and, in the case where the management device 20 is connected to the test device 10 or a user changes the settings of the test device 10, the password should be input to ensure security in connection to the test device 10 as well as change of the settings of the test device 10. As a result, it is possible to prevent the settings of the management system from being altered by a third party other than a manager who connects to the test device 10.

Further, when the control part 13 receives information regarding identifiers for respective test devices 10 from the management device 20, each of the identifiers is indicated on an indication part 15 of each of the test devices 10, and the user may distinguish the respective test devices 10 through the identifiers.

The management device 20 may be a device having a management program to manage a plurality of test devices 10. The management program is a program that manages a plurality of test devices 10 registered on a network of the management system and may be a software program or application, wherein: analysis information of various biomaterials transmitted from the test devices 10 are received and managed separately for the test devices 10; whether the software has updated software information present in each of the test devices 10 may be periodically confirmed, in turn enabling a current version of the software in each test device 10 to be maintained; and integrated management is performed, for example, in the case where each test device 10 has operational errors or mechanically malfunctions, such a condition is sensed and a notification of the sensed condition may be provided to the user. However, functions of the management program are not particularly limited thereto.

The management device 20 may be an apparatus such as a PC or server having such a management program as described above.

For distinguishing respective test devices 10, the management device 20 may assign unique identifiers to a plurality of test devices 10 to distinguish the test devices 10 from one another. When the management device 20 provides an identifier to each of the test devices 10, the test device 10 may have the identifier assigned by the management device 20, which is present on an indication part 15. By placing the identifier on the indication part 15 to display the same, it is possible to easily identify a test device 10 needed for checking among the plural test devices 10, in the case where the user inspects an analysis result from the test device 10 or a variety of information transmitted from the management device 20 to the test device 10.

In this regard, the identifier may be an inherent mark endowed to each test device 10. For instance, if ten (10) blood testers of the same type have been registered in the management system, the blood testers have identifiers in alphabets (English letters) such as a, b, c, d, e, f, g, h, i and j, assigned thereto and each of the assigned identifiers is displayed on an indication part 15 of each blood tester, thus enabling the 10 blood testers to be distinguished from one another. When the user wishes to check an analysis result of a specific blood tester having the identifier 'a' assigned thereto by the management device 20, the analysis result can be successfully confirmed or obtained by searching for the test device 10 having the identifier 'a' in the management device 20, without remembering alternative instrument serial numbers or other marks to indicate the foregoing blood tester. If information informing of operational error occurring in the test device 10 having the identifier 'b' assigned thereto in the management device 20 is indicated, it is not necessary to remember alternative instrument serial numbers or other marks to indicate the foregoing test device 10 even when the test device 10 experiencing an operational error is searched for from a plurality of test devices 10. Instead, it is sufficient to locate the test device 10 having the identifier 'b' by inspecting each identifier present on an indication part 15 of each of the test devices 10. Here, letters were used as an illustrative example of the identifiers, however, the present invention is not particularly limited thereto.

Hereinafter, the following description will be given of a management method of plural test devices 10 including providing identifiers to respective test devices 10, to enable the test devices 10 to be distinguished from one another.

Figure 3:
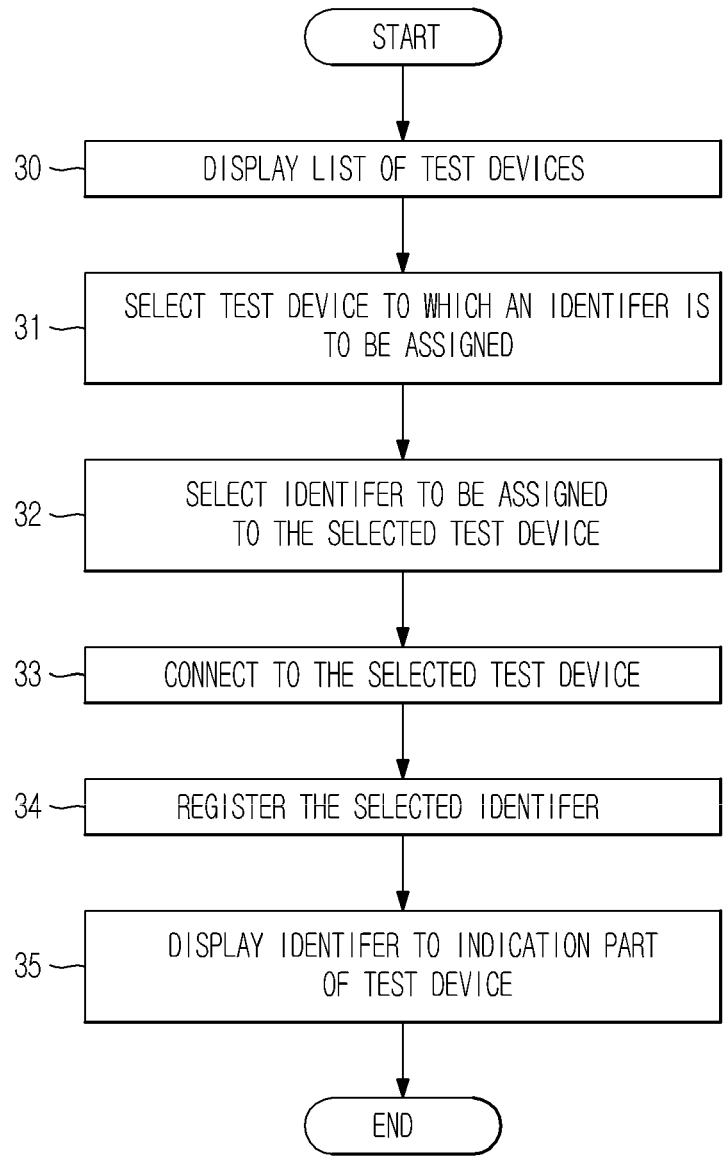
FIG. 3 is a flow diagram illustrating a management method of a test device according to an exemplary embodiment.

FIG. 3 is a flow diagram illustrating a management method of a test device 10 according to an exemplary embodiment.

As shown in FIG. 3, a list of test devices 10 present on a network of a management system is initially displayed on an indication part of the management device 20 (operation 30). By scanning the network of the management system, the test devices connected to the network are found, and then, the list of the test devices connected to the network is displayed on the indication part of the management device. When the list of the test devices 10 connected to the network is displayed on the indication part, a specific test device 10 to be distinguished from the other test devices 10 is selected by providing an identifier thereto (operation 31).

After selecting the test device 10, an identifier assigned to the selected test device 10 may be selected (operation 32). In this case, the identifier may be any mark capable of distinguishing the test device 10, which has the identifier assigned thereto, from the other test devices 10. The identifier may be English letters, numerals, symbols, Korean characters, or the like.

After selecting the identifier to be assigned to the test device 10, the management device 20 attempts to contact the test device 10 and transmit information regarding the selected identifier to the test device 10 (operation 33). In such a process, inputting a password previously allocated to each test device 10 or changing settings thereof may be demanded. If a password identical to the original password of the test device 10 is input, connection to the test device 10 may be permitted, in turn imparting the selected identifier to the same. This process may effectively prevent settings of a management system from being randomly altered by a third party other than the user of the test device 10 or a manager of the management system.

After completing connection to the test device 10, the test device 10 may receive information regarding identifiers and recognize the selected identifier as its identifier, in turn registering the identifier (operation 34). According to the foregoing procedures, each of the plural test devices 10 may have respective identifiers assigned thereto, which in turn are registered in the management system.

When the identifier is registered in the test device 10, the test device 10 displays the assigned identifier on an indication part 15 (operation 35). The identifier displayed on the indication part 15 of the test device 10 may be continuously indicated (on the indication part 15 of the test device 10), thus enabling the foregoing test device 10 to be distinguished from the others, unless the identifier is changed into another mark through provision of the identifier described above.

Figure 4:
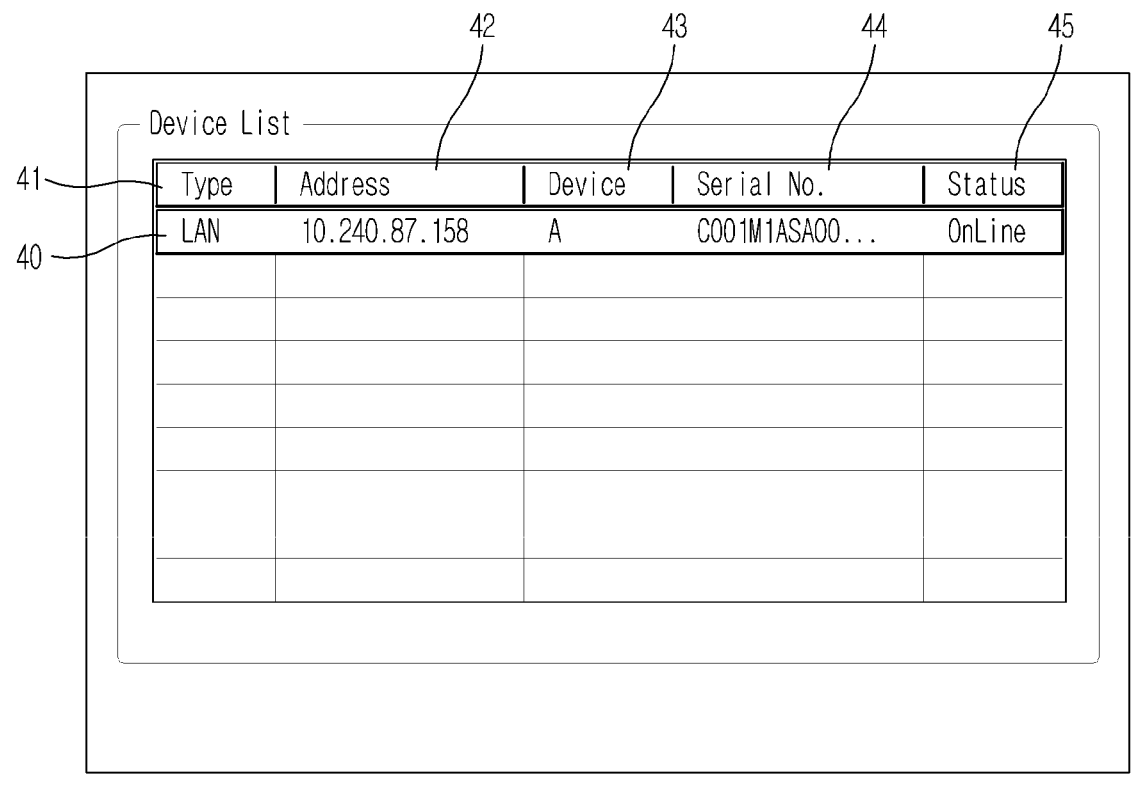

FIG. 4 illustrates provision of an identifier to a test device 10 present on a network of a management system according to an exemplary embodiment.

As illustrated in FIG. 4, the management device 20 may have a list of devices connected to a network of a management system, which is displayed on an indication part of the management device 20. Here, FIG. 4 shows only one device connected to the network, as an illustrative example. While indicating a list of test devices 10, information regarding such test devices 10 may also be displayed (operation 40). In particular, FIG. 4 illustrates a variety of information, for example; a communication mode 41 between the test device 10 and the management device 20 (i.e., LAN), an address 42 of the test device 10, a serial number 44 of the test device 10, a present connection state on the network 45 (i.e., online), etc. In addition to the foregoing information, an identifier 'A' assigned to a corresponding test device 10 is illustratively shown in FIG. 4 (operation 43). As described above, the identifier assigned to the test device 10 may be set in various modes. The configuration of the indication part shown in FIG. 4 is only an illustrative example and is not particularly limited thereto.

As such, when the management device 20 selects an identifier to be assigned to a test device 10 and connects with the test device 10 to register the corresponding identifier in the test device 10, the test device 10 may display the registered identifier on an indication part 15 thereof.

Figure 5:
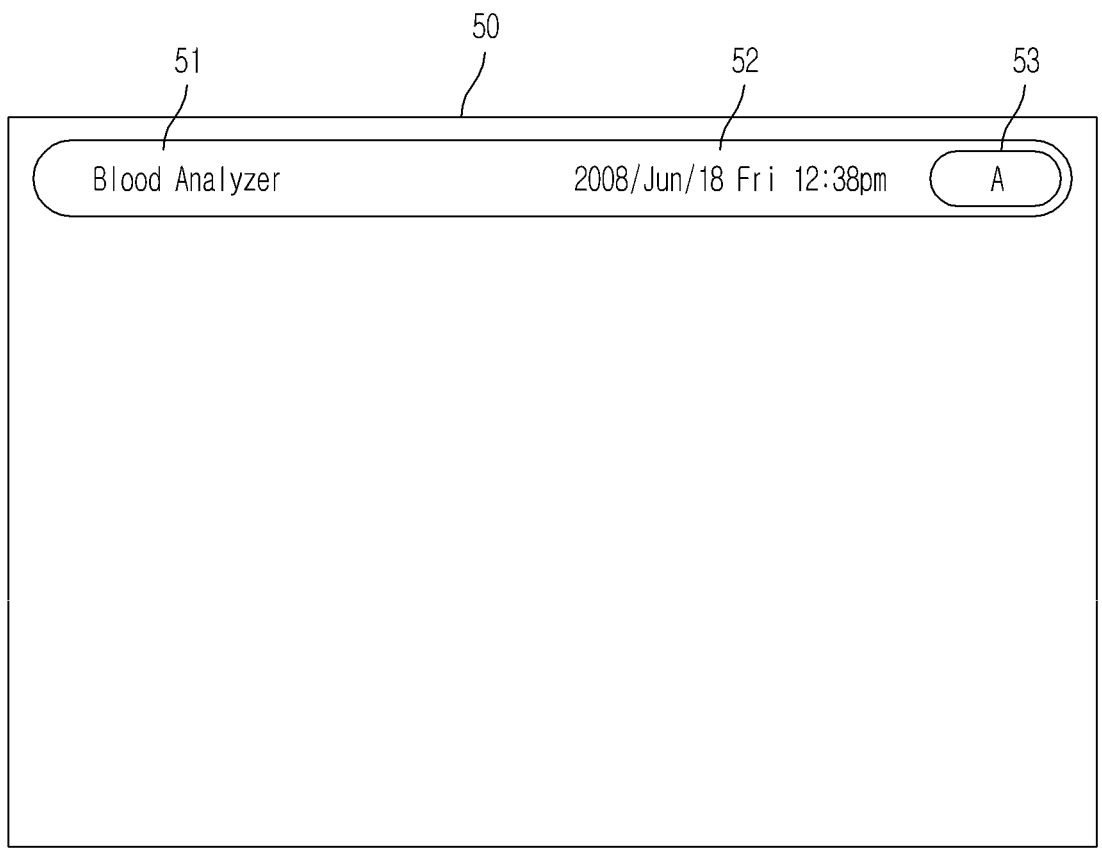
FIG. 5 illustrates indication of a test device with an identifier according to an exemplary embodiment.

FIG. 5 illustrates an indication part 15 of a test device 10 having an identifier according to an exemplary embodiment.

As shown in FIG. 5, an identifier 'A' 53 assigned to the test device 10 is displayed together with a type of the test device 51 and date information 52 in an information display area 50 at the upper end of the indication part 15. As such, by displaying the identifier on the indication part 15, a user can distinguish a plurality of test devices 10 from one another through identifiers thereof. The configuration of the indication part 15 shown in the figure is only an illustrative example and is not particularly limited thereto.

Although the exemplary embodiments have been described above with reference to the accompanying drawings, it is clearly understood that the exemplary embodiments do not particularly restrict the scope of the present disclosure. Accordingly, it would be appreciated by those skilled in the art that various substitutions, variations and/or modifications may be made in these embodiments without departing from the principles and spirit of the disclosure. Therefore, it is understood that the present disclosure is not restricted to the technical configurations and arrangements illustrated above.

What is claimed is:

1. A management system for managing a plurality of test devices, comprising:
   a management device configured to receive a first user input of a first identifier and assign the first identifier to a first test device among the plurality of test devices, and configured to receive a second user input of a second identifier and assign the second identifier to a second test device among the plurality of test devices,
   wherein the first test device displays the first identifier and the second test device displays the second identifier, and
   wherein the first test device displays the first identifier on an indication part of the first test device and the second test device displays the second identifier on an indication part of the second test device.

2. The management system according to claim 1, wherein the management device stores a management program to manage the plurality of test devices.

3. The management system according to claim 2, wherein the first identifier is different from the second identifier and the first identifier and the second identifier are registered in the management device by the management program.

4. The management system according to claim 1, wherein the first identifier and the second identifier are marks that distinguish the first test device from the second test device.

5. The management system according to claim 1, wherein the first test device or the second test device is a testing device that analyzes a biomaterial.

6. The management system according to claim 1, wherein communication between the management device and the plurality of test devices is executed by at least one of Bluetooth, infrared communication, Wi-Fi, wired or wireless communication over a network, Serial, ZigBee, radio frequency, and universal serial bus.

7. A method of managing a plurality of test devices, the method comprising:
    selecting, by a management system, a test device present on a network of the management system;
    receiving a user input of an identifier;
    providing the identifier to the selected test device;
    associating the provided identifier with identification information of the test device; and
    storing the associated information in the management system,
    wherein the test device displays the identifier assigned to the test device on an indication part of the test device.

8. The method according to claim 7, wherein the selecting comprises:
    locating the test device on the network, wherein the identifier is a unique identifier.

9. The method according to claim 7, wherein the selecting comprises:
    connecting to the test device,
    wherein the providing comprises providing the identifier to the connected test device.

10. The method according to claim 9, wherein connecting comprises:
    attempting a connection to the test device;
    requesting input of a password; and
    in response to receiving the requested password, permitting the connection to the test device.

11. The method according to claim 10, wherein the password is a secret code that is requested to be input when settings of the test device are changed.

12. The management system according to claim 1, wherein the first test device is assigned a first serial number different than the first identifier and the second test device is assigned a second serial number different than the second identifier.

13. The method according to claim 7, wherein the identification information is a serial number of the test device.

* * * * *